United States Patent [19]

Graham et al.

[11] Patent Number: 5,480,893
[45] Date of Patent: * Jan. 2, 1996

[54] INHIBITORS OF FARNESYL PROTEIN TRANSFERASE

[75] Inventors: Samuel L. Graham, Schwenksville; S. Jane deSolms, Norristown, both of Pa.

[73] Assignee: Merck & Co., Inc., Rahway, N.J.

[*] Notice: The portion of the term of this patent subsequent to Jul. 5, 2011, has been disclaimed.

[21] Appl. No.: 242,575

[22] Filed: May 13, 1994

Related U.S. Application Data

[62] Division of Ser. No. 768,798, Sep. 30, 1991, Pat. No. 5,340,828.

[51] Int. Cl.$^6$ .................. A61K 31/44; A61K 31/415; C07D 313/04

[52] U.S. Cl. .................. 514/336; 514/357; 514/399; 514/562; 514/450; 514/459; 514/461; 514/432; 549/271; 549/293; 549/295; 549/28; 549/9; 549/59; 549/65; 546/268; 546/283; 546/284; 548/311.1; 548/315.1; 548/315.4; 530/331

[58] Field of Search .................. 530/331; 514/357, 514/399, 562, 450, 459, 461, 18, 432, 336; 549/271, 293, 295, 28, 9, 65, 59; 548/311.1, 315.1, 315.4; 546/284, 268, 283

[56] References Cited

U.S. PATENT DOCUMENTS

| | | | |
|---|---|---|---|
| 4,801,609 | 1/1989 | Haslanger et al. | 514/513 |
| 4,855,286 | 8/1989 | Wagner et al. | 514/19 |
| 4,879,309 | 11/1989 | Doll et al. | 514/513 |
| 4,929,641 | 5/1990 | Haslanger et al. | 514/506 |
| 4,931,591 | 6/1990 | Buhlmayer et al. | 564/165 |
| 4,977,277 | 12/1990 | Rosenberg et al. | 549/215 |
| 5,043,268 | 8/1991 | Stock | 435/15 |
| 5,081,284 | 1/1992 | Higuchi et al. | 560/159 |
| 5,326,773 | 7/1994 | deSolms et al. | 514/336 |
| 5,340,828 | 8/1994 | Graham et al. | 514/357 |

FOREIGN PATENT DOCUMENTS

| | | |
|---|---|---|
| 0322184 | 6/1989 | European Pat. Off. . |
| 0456180 | 11/1991 | European Pat. Off. . |
| 0461869A | 12/1991 | European Pat. Off. . |
| WO91/16340 | 10/1991 | WIPO . |

OTHER PUBLICATIONS

Goldstein, J. L. et al., Nonfarnesylated Tetrapeptide Inhibitors of Protein Farnesyltransferase*, (1991), Jour. of Biol. Chem., 266, pp. 15575–15578.

Reiss, Y., et al., Sequence requirement for peptide recognition by rat brain p21ras protein farnesyltransferase (1991), Proc. Natl. Acad. Sci., USA, 88, pp. 732–736.

Kohl, N. E. et al., "Protein farnesyltransferase inhibitors block the growth of ras-dependent tumors in nude mice", Proc. Natl. Acad. Sci., USA, vol. 91, pp. 9141–9145, (1994).

*Primary Examiner*—C. Warren Ivy
*Assistant Examiner*—A. A. Owens
*Attorney, Agent, or Firm*—David A. Muthard; Mark R. Daniel

[57] ABSTRACT

The present invention is directed to compounds which inhibit farnesyl-protein transferase (FTase) and the farnesylation of the oncogene protein Ras. The invention is further directed to chemotherapeutic compositions containing the compounds of this invention and methods for inhibiting farnesyl-protein transferase and the farnesylation of the oncogene protein Ras.

12 Claims, No Drawings

INHIBITORS OF FARNESYL PROTEIN TRANSFERASE

This is a division of application Ser. No. 07/768,798, filed Sep. 30, 1991 now U.S. Pat. No. 5,340,828.

BACKGROUND OF THE INVENTION

The Ras gene is found activated in many human cancers, including colorectal carcinoma, exocrine pancreatic carcinoma, and myeloid leukemias. Biological and biochemical studies of Ras action indicate that Ras functions like a G-regulatory protein, since Ras must be localized in the plasma membrane and must bind with GTP in order to transform cells (Gibbs, J. et al., *Microbiol. Rev.* 53:171–286 (1989). Forms of ras in cancer cells have mutations that distinguish the protein from Ras in normal cells.

At least 3 post-translational modifications are involved with Ras membrane localization, and all 3 modifications occur at the C-terminus of Ras. The Ras C-terminus contains a sequence motif termed a "CAAX" or "Cys-Aaa$^1$-Aaa$^2$-Xaa" box (Aaa is an aliphatic amino acid, the Xaa is any amino acid) (Willumsen et al., *Nature* 310:583–586 (1984)). Other proteins having this motif include the Ras-related GTP-binding proteins such as Rho, fungal mating factors, the nuclear lamins, and the gamma subunit of transducin.

Farnesylation of Ras by the isoprenoid farnesyl pyrophosphate (FPP) occurs in vivo on Cys to form a thioether linkage (Hancock et al., *Cell* 57:1167 (1989); Casey et al., *Proc. Natl. Acad. Sci. USA* 86:8323 (1989)). In addition, Ha-Ras and N-Ras are palmitoylated via formation of a thioester on a Cys residue near a C-terminal Cys farnesyl acceptor (Gutierrez et al., *EMBO J.* 8:1093–1098 (1989); Hancock et al., *Cell* 57:1167–1177 (1989)). Ki-Ras lacks the palmitate acceptor Cys. The last 3 amino acids at the Ras C-terminal end are removed proteolytically, and methyl esterification occurs at the new C-terminus (Hancock et al., ibid). Fungal mating factor and mammalian nuclear lamins undergo identical modification steps (Anderegg et al., *J. Biol. Chem.* 263:18236 (1988); Farnsworth et al., *J. Biol. Chem.* 264:20422 (1989)).

Inhibition of Ras farnesylation in vivo has been demonstrated with lovastatin (Merck & Co., Rahway, N.J.) and compactin (Hancock et al., ibid; Casey et al., ibid; Schafer et al., *Science* 245:379 (1989)). These drugs inhibit HMG-CoA reductase, the rate limiting enzyme for the production of polyisoprenoids and the farnesyl pyrophosphate precursor. It has been shown that a farnesyl-protein transferase using farnesyl pyrophosphate as a substrate is responsible for Ras farnesylation. (Reiss et al., *Cell*, 62: 81–88 (1990); Schaber et al., *J. Biol. Chem.*, 265:14701–14704 (1990); Schafer et al., Science, 249: 1133–1139 (1990); Manne et al., *Proc. Natl. Acad. Sci USA*, 87: 7541–7545 (1990)).

Inhibition of farnesyl-protein transferase and, thereby, of farnesylation of the Ras protein, blocks the ability of Ras to transform normal cells to cancer cells. The compounds of the invention inhibit Ras farnesylation and, thereby, generate soluble Ras which, as indicated infra, can act as a dominant negative inhibitor of Ras function. While soluble Ras in cancer cells can become a dominant negative inhibitor, soluble Ras in normal cells would not be an inhibitor.

A cytosol-localized (no Cys-Aaa$^1$-Aaa$^2$-Xaa box membrane domain present) and activated (impaired GTPase activity, staying bound to GTP) form of Ras acts as a dominant negative Ras inhibitor of membrane-bound Ras function (Gibbs et al., *Proc. Natl. Acad. Sci. USA* 86:6630–6634(1989)). Cytosollocalized forms of Ras with normal GTPase activity do not act as inhibitors. Gibbs et al., ibid, showed this effect in Xenopus oocytes and in mammalian cells.

Administration of compounds of the invention to block Ras farnesylation not only decreases the amount of Ras in the membrane but also generates a cytosolic pool of Ras. In tumor cells having activated Ras, the cytosolic pool acts as another antagonist of membrane-bound Ras function. In normal cells having normal Ras, the cytosolic pool of Ras does not act as an antagonist. In the absence of complete inhibition of farnesylation, other farnesylated proteins are able to continue with their functions.

Farnesyl-protein transferase activity may be reduced or completely inhibited by adjusting the compound dose. Reduction of farnesyl-protein transferase enzyme activity by adjusting the compound dose would be useful for avoiding possible undesirable side effects such as interference with other metabolic processes which utilize the enzyme.

These compounds and their analogs are inhibitors of farnesyl-protein transferase. Farnesyl-protein transferase utilizes farnesyl pyrophosphate to covalently modify the Cys thiol group of the Ras CAAX box with a farnesyl group. Inhibition of farnesyl pyrophosphate biosynthesis by inhibiting HMG-CoA reductase blocks Ras membrane localization in vivo and inhibits Ras function. Inhibition of farnesyl-protein transferase is more specific and is attended by fewer side effects than is the case for a general inhibitor of isoprene biosynthesis.

Previously, it has been demonstrated that tetrapeptides with the CAAX sequence inhibit Ras farnesylation (Schaber et al., ibid; Reiss et al., ibid; Reiss et al., *PNAS*, 88:732–736 (1991)). However, the reported inhibitors of farnesyl-transferase are metabolically unstable or inactive in cells.

The compounds of the present invention, which contain one or more reduced peptide bonds, and are capable of forming a 5- or 6- membered lactone or thiolactone ring, are inhibitors of Ras farnesyl-transferase. The presence of the reduced amide linkage confers metabolic stability to these inhibitors such that they are capable of inhibiting Ras farnesylation in vivo. Reduction of these amide bonds leads to an unexpected enhancement of intrinsic enzyme-inhibitory activity. In addition, the lactone forms of these inhibitors are prodrugs that efficiently deliver the more active parent hydroxy or mercapto acids to the intracellular compartment that is the site of Ras farnesylation.

It is, therefore, an object of this invention to develop compounds which will inhibit farnesyl-protein transferase and the farnesylation of the oncogene protein Ras. It is a further object of this invention to develop chemotherapeutic compositions containing the compounds of this invention, and methods for producing the compounds of this invention.

SUMMARY OF THE INVENTION

The present invention includes compounds which inhibit farnesyl-protein transferase and the farnesylation of the oncogene protein Ras, chemotherapeutic compositions containing the compounds of this invention, and methods for producing the compounds of this invention.

The compounds of this invention are illustrated by the formula:

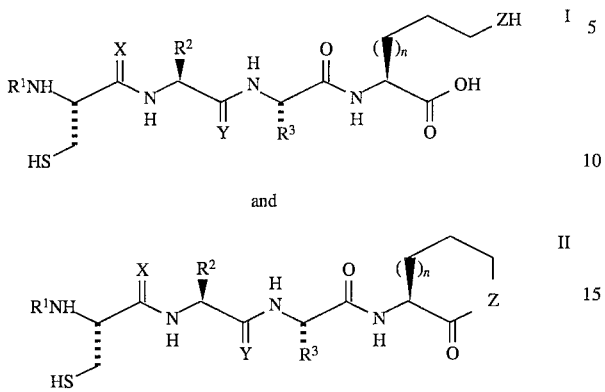

DETAILED DESCRIPTION OF THE INVENTION

The compounds of this invention are useful in the inhibition of farnesyl-protein transferase and the farnesylation of the oncogene protein Ras. In a first embodiment of this invention, the compounds are illustrated by the formula:

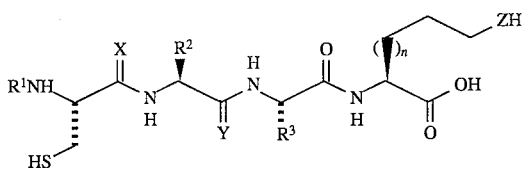

wherein:

X or Y are independently $H_2$ or O, provided that at least one of these is $H_2$;

$R^1$ is H, an alkyl group, an acyl group, an alkylsulfonyl group or arylsulfonyl group, wherein the alkyl and the alkyl portion of the acyl is a straight chain or branched chain hydrocarbons of 1 to 6 carbons atoms, or in the alternative $R^1NH$ may be absent;

$R^2$ and $R^3$ are the side chains of naturally occurring amino acids, or in the alternative may be substitued or unsubstitued aliphatic, aromatic or heterocyclic groups, such as allyl, cyclohexyl, phenyl, pyridyl, imidazolyl or saturated chains of 2 to 8 carbon atoms, wherein the aliphatic substitutients may be substituted with an aromatic or heteroaromatic ring;

Z is O or S; and n is 0, 1, or 2;

or the pharmaceutically acceptable salts thereof.

In a second embodiment of this invention, the compounds are illustrated by the formula:

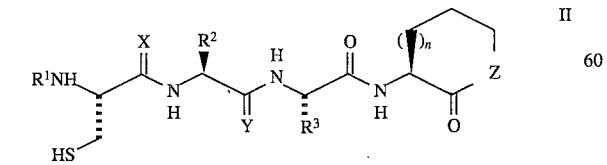

wherein:

X or Y are independently $H_2$ or O, provided that at least one of these is $H_2$;

$R^1$ is H, an alkyl group, an acyl group, an alkylsulfonyl group or arylsulfonyl group, wherein alkyl and acyl groups comprise straight chain or branched chain hydrocarbons of 1 to 6 carbon atoms, or in the alternative $R^1NH$ may be absent;

$R^2$ and $R^3$ are the side chains of naturally occurring amino acids, or in the alternative may be substituted or unsubsituted aliphatic, aromatic or heterocyclic groups, such as allyl, cyclohexyl, phenyl, pyridyl, imidazolyl or saturated chains of 2 to 8 carbon atoms, wherein the aliphatic substituents may also be substituted with an aromatic or heteroaromatic ring;

Z is O or S; and n is 0, 1, or 2;

or the pharmaceutically acceptable salts thereof.

The preferred compounds of this invention are as follows:

N-(2(R)-amino-3-mercaptopropyl)isoleucyl-phenylalanyl-homoserine,

N-(2(R)-amino-3-mercaptopropyl)isoleucyl-isoleucylhomoserine,

N-(2(R)-amino-3-mercaptopropyl)isoleucyl-phenylalanyl-homoserine lactone,

N-(2(R)-amino-3-mercaptopropyl)isoleucyl-isoleucylhomoserine lactone,

N-(2(R)-amino-3-mercaptopropyl)isoleucyl-phenylalanyl-homocysteine lactone,

N-[2(S)-(2(R)-amino-3-mercaptopropylamino)-3(S)-methylpentyl]isoleucyl-homoserine lactone, N-[N'-(2(R)-amino-3-mercaptopropyl)isoleucyl-phenylalanyl] -3(S)-amino-tetrahydropyran-2-one, N-[N'-(2(R)-amino-3-mercaptopropyl)isoleucyl-isoleucyl] -3(S)-amino-tetrahydropyran-2-one, N-(2(R)-amino-3-mercaptopropyl)isoleucyl-isoleucylhomocysteine lactone, N-[2(S)-(2(R)-amino-3-mercaptopropylamino)-3(S)-methylpentyl]isoleucyl-homoserine, N-[N'-(2(R)-amino-3-mercaptopropyl)isoleucyl-phenylalanyl]-3(S)-amino-4-hydroxypentanoic acid, or N-[N'-(2(R)-amino-3-mercaptopropyl)isoleucylisoleucyl]- 3(S)-amino-4-hydroxypentanoic acid.

The most preferred compounds of this invention are as follows:

N-[2(S)-(2(R)-amino-3-mercaptopropylamino)-3(S)-methylpentyl]isoleucyl-homoserine

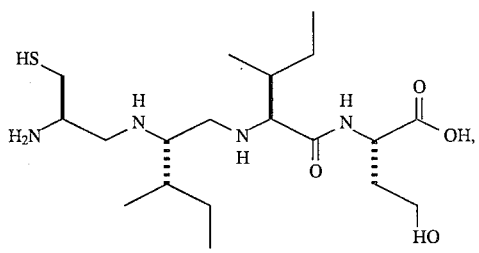

N-[2(S)-(2(R)-amino-3-mercaptopropylamino)-3(S)-methylpentyl]isoleucyl-homoserine lactone

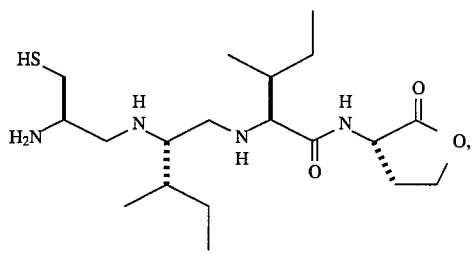

N-[N'-(2(R)-amino-3-mercaptopropyl)isoleucyl-isoleucyl]-3(S)-amino-4-hydroxy-pentanoic acid, or

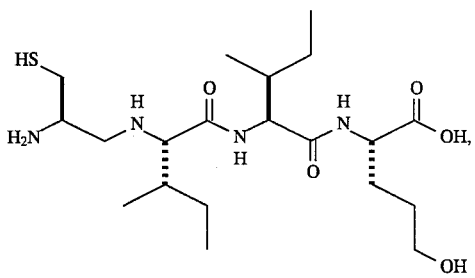

N-[N'(2(R)-amino-3-mercaptopropyl)isoleucyl-isoleucyl]-3(S)-aminotetrahydropyran-2-one.

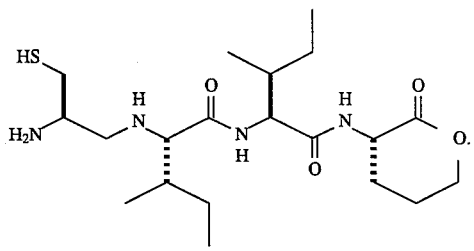

In the present invention, the amino acids are identified both by conventional 3 letter and single letter abbreviations as indicated below:

| Alanine | Ala | A |
| Arginine | Arg | R |
| Asparagine | Asn | N |
| Aspartic acid | Asp | D |
| Asparagine or Aspartic acid | Asx | B |
| Cysteine | Cys | C |
| Glutamine | Gln | Q |
| Glutamic acid | Glu | E |
| Glutamine or Glutamic acid | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The pharmaceutically acceptable salts of the compounds of this invention include the conventional non-toxic salts of the compounds of this invention as formed, e.g., from non-toxic inorganic or organic acids. For example, such conventionl non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, and the like.

The pharmaceutically acceptable salts of the compounds of this invention can be synthesized from the compounds of this invention which contain a basic moiety by conventional chemical methods. Generally, the salts are prepared by reacting the free base with stoichiometric amounts or with an excess of the desired salt-forming inorganic or organic acid in a suitable solvent or various combinations of solvents.

The pharmaceutically acceptable salts of the acids of the compounds of this invention are also readily prepared by conventional procedures such as treating an acid of the compounds of this invention with an appropriate amount of a base, such as an alkali or alkaline earth metal hydroxide e.g. sodium, potassium, lithium, calcium, or magnesium, or an organic base such as an amine, e.g., dibenzylethylenediamine, trimethylamine, piperidine, pyrrolidine, benzylamine and the like, or a quaternary ammonium hydroxide such as tetramethylammonium hydroxide and the like.

The compounds of the invention can be synthesized from their constituent amino acids by conventional peptide synthesis techniques, and additional method described below. Standard methods of peptide synthesis are disclosed, for example, in the following works: Schroeder et al., "The Peptides", Vol. I, Academic Press 1965, or Bodanszky et al., "Peptide Synthesis", Interscience Publishers, 1966, or McOmie (ed.) "Protective Groups in Organic Chemistry", Plenum Press, 1973, or Barany et al., "The Peptides: Analysis, Synthesis, Biology" 2, Chapter 1, Academic Press, 1980, or Stewart et al., "Solid Phase Peptide Synthesis", Second Edition, Pierce Chemical Company, 1984. The teachings of these works are hereby incorporated by reference.

The compounds of this invention are prepared according to the reaction Schemes as set forth below:

SCHEME 1

Reaction A
Coupling of residues to form an amide bond

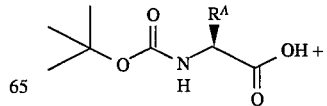

-continued
SCHEME 1

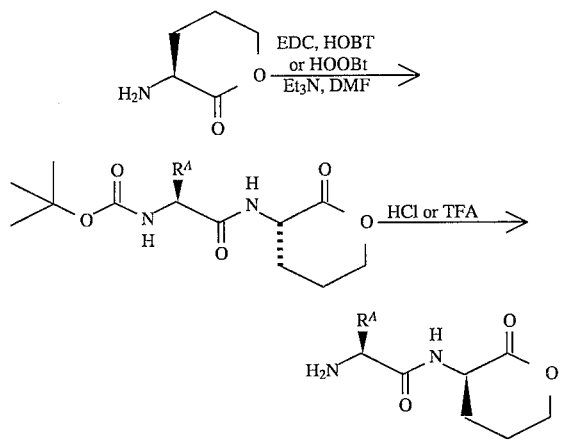

SCHEME 2

Reaction B
Preparation of reduced dipeptides from peptides

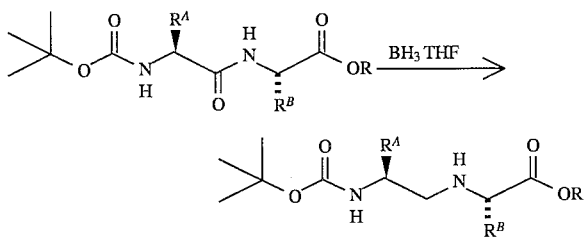

SCHEME 3

Reaction C
Preparation of reduced peptide units by reductive amination

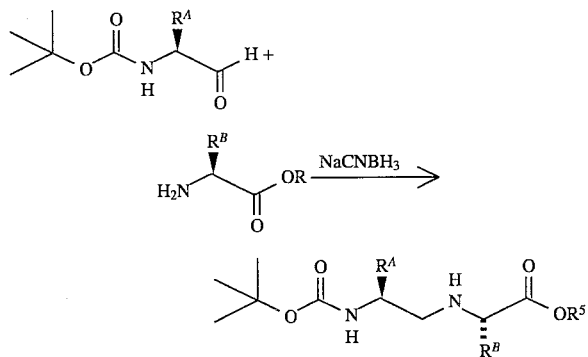

Compounds of this invention are prepared by employing reactions A–C as shown in Schemes 1–3 above, in addition to other standard manipulations such as ester hydrolysis, cleavage of peptide protecting groups, etc., as may be known in the literature or exemplified in the Examples. The key bond-forming reactions are as follows:

Reaction A. Peptide bond formation and protecting group cleavage using standard solution or solid phase methodologies.

Reaction B. Preparation of a reduced subunit by borane reduction of the amide moiety.

Reaction C. Preparation of a reduced peptide subunit by reductive alkylation of an amine by an aldehyde using sodium cyanoborohydride, hydrogen and a catalyst or other reducing agents.

These reactions may be employed in a linear sequence to provide the compounds of the invention or they may be used to synthesize dipeptide fragments which are subsequently joined by the alkylation or acylation reactions described in the Schemes.

The compounds of this invention inhibit farnesyl-protein transferase and the farnesylation of the oncogene protein Ras. These compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, and myeloid leukemias.

The compounds of this invention may be administered to mammals, preferably humans, either alone or, preferably, in combination with pharmaceutically-acceptable carriers or diluents, optionally with known adjuvants, such as alum, in a pharmaceutical composition, according to standard pharmaceutical practice. The compounds can be administered orally or parenterally, including intravenous, intramuscular, intraperitoneal, subcutaneous, rectal and topical administration.

For oral use of a chemotherapeutic compound according to this invention, the selected compounds may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The present invention also encompasses a pharmaceutical composition useful in the treatment of cancer, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g. saline, at a pH level, e.g., 7.4. The solutions may be introduced into a patient's intramuscular blood-stream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a human patient undergoing treatment for cancer. Administration occurs in an amount between about 0.1 mg/kg of body weight to about 20 mg/kg of body weight of a mammal per day, preferably of between 0.5 mg/kg of body weight to about 10 mg/kg of body weight of a mammal per day.

EXAMPLES

Examples provided are intended to assist in a further understanding of the invention. Particular materials employed, species and conditions are intended to be further illustrative of the invention and not limitative of the reasonable scope thereof.

EXAMPLE 1

Preparation of N-(2(R)-Amino-3-mercaptopropyl)isoleucyl-phenylalanyl-homoserine lactone and N-(2(R)-Amino-3-mercaptopropyl)isoleucyl-phenylalanyl-homoserine Step A: Preparation of (t-Butoxycarbonyl)phenylalanylhomoserine lactone To a solution of N-t-butoxycarbonylphenylalanine (1.69 g, 6.39 mmol) in $CH_2Cl_2$ (10 mL) and EtOAc (10 mL) were added 3,4-dihydro-3-hydroxy-4-oxo-1,2,3-benzotriazine (HOOBT, 1.04 g, 6.39 mmol) and 1-ethyl-3-(3-dimethylamino-propyl)carbodiimide (EDC, 1.23 g, 6.39 mmol ) followed by the hydrochloride salt homoserine lactone (0.80 g, 5.81 mmol ). The pH was adjusted to 6.5–7.0 with N,N-diisopropylethylamine (1.11 mL, 6.39 mmol) and the mixture was stirred at ambient temperature for 16 hours. The mixture was concentrated and the residue was partitioned between EtOAc (100 mL) and $H_2O$ (50 mL). The organic layer was washed with 10% citric acid (1×25 mL), saturated $NaHCO_3$ (1×25 mL), brine (1×25 mL), dried ($Na_2SO_4$), filtered, and concentrated. The crude product was purified by chromatography (silica gel, $CH_2Cl_2$: MeOH, 98:2) to give 1.4 g of the title compound.

Step B: Phenylalanyl-homoserine lactone hydrochloride salt

The product of Step A (1.4 g, 4.02 mmol) was dissolved in EtOAc (40 mL), cooled to −25° C., and treated with gaseous HCL (10 min. ) followed by nitrogen (10 min.) to remove excess HCl. The solvent was evaporated to give 1.14 g of the title compound.

Step C: Preparation of N-(t-butoxycarbonyl)-S-triphenylmethylcyteine aldehyde

This compound was synthesized by applying the procedure of Goel, Krolls, Stier, and Kesten to N-(t-butoxycarbonyl)-S-trityl cysteine (Org. Synthesis 67, 69 (1988). The compound was obtained as a white solid, which was used without purification. $^1H$ NMR ($CDCl_3$) δ 9.2 (1H, s), 7.5–7.1 (18H, m), 5.1 (1H, br d), 3.92 (1H, m), 2.85–2.5 (2H, m), 1.4 (9H, s).

Step D: N-[(2R)-(t-Butoxycarbonylamino)-3-triphenylmethyl mercaptopropyl]isoleucine Isoleucine (1.97 g, 0.015 mol) was suspended in EtOH (150 mL) with N-t-butoxycarbonyl-S-triphenylmethylcysteine aldehyde (6.71 g, 0.015 mol) and 3A molecular sieves. Sodium cyanoborohydride (0.47 g, 0.0075 mol) was added and the mixture was stirred at ambient temperature for 72 hours. Filtration and concentration gave an oil, which was chromatographed (silica gel, $CH_2Cl_2$: MeOH, 95:5to 9:1) to give 2.1 g of the title compound, mp 83°–90° C. $^1H$ NMR ($CDCl_3$) δ 7.19–7.41 (m, 15H), 4.98–5.12 (m, 1H), 3.58–3.70 (m, 2H), 3.18 (br s, 1H), 2.78–2.81 (m, 2H), 2.32–2.60 (m, 2H), 1.80–1.96 (m, 1H), 1.40 (s, 9H), 1.20–1.35 (m, 1H), 0.84–0.93 (m, 6H).

Step E: N-[2(R)-(t-Butoxycarbonyl)amino-3-(triphenylmethyl)mercaptopropyl]isoleucyl-phenylalanyl-homoserine lactone N-[2(R)-(t-butoxycarbonyl)amino-3-(triphenylmethyl)mercaptopropyl]isoleucine (0.30 g, 0.53 mmol), dissolved in $CH_2Cl_2$ (10 mL) and EtOAc (10 mL), was treated with HOOBT (96 mg, 0.59 mmol), EDC (0.112 g, 0.59 mmol), and phenylalanyl-homoserine lactone hydrochloride salt (0.167 g, 0.59 mmol). The pH was adjusted to 6.5–7.0 with N,N-diisopropylethylamine (0.102 mL, 0.59 mmol) and the mixture was stirred at ambient temperature for 16 hours. The mixture was concentrated and the residue was partitioned between EtOAc (30 mL) and $H_2O$ (15 mL). The organic layer was washed with 10% citric acid (1×15 mL), saturated $NaHCO_3$ (1×15 mL), brine (1×15 mL), and dried ($Na_2SO_4$). Filtration and concentration gave the crude product, which was chromatographed twice (silica gel, $CH_2Cl_2$: MeOH, 98:2; silica gel, EtOAc: hexane, 2:1) to provide 0.115 g of the title compound.

Step F: N-(2(R)-Amino-3-mercaptopropyl)isoleucylphenylalanyl-homoserine lactone

The product of Step E was dissolved in $CH_2Cl_2$ (2 mL) and trifluoroacetic acid (1 mL) was added followed by triethylsilane (0.093 mL, 0.58 mmol). The mixture was stirred at ambient temperature for 1 h, concentrated, and the residue was triturated with $Et_2O$ to give 0.078 g of pure title compound, m.p. 103°–105° C. 1H NMR (DMSO) δ8.75 (d,J=9 Hz, 1H), 7.34–7.17 (m, 5H), 4.75–4.53 (m, 2H), 4.43 (t, J=18 Hz, 1H), 4.28–4.16 (m, 1H), 3.30–3.16 (m, 1H), 3.04 (dd,J=12,14 Hz, 1H), 2.85 (dd,J=12,14 Hz, 1H), 2.75–2.33 (m, 7H), 2.20–2.05 (m, 1H), 1.66–1.42 (m, 2H), 1.16–1.00 (m, 1H), 0.89–0.70 (m, 6H ). Anal. Calcd for $C_{22}H_{34}N_4O_4S.2CF_3CO_2H$: C, 46.02; H, 5.35; N, 8.26. Found: C, 46.19; H, 5.23; N, 8.41.

Step G: N-(2(R)-Amino-3-mercaptopropyl)isoleucylphenylalanyl-homoserine

N-(2(R)-Amino-3-mercaptopropyl)isoleucylphenylalanyl-homoserine lactone (0.003 g, 0.004 mmol) was dissolved in MeOH (0.1 mL) and 1N NaOH (0.013 mL) was added followed by MeOH (0.305 mL). Conversion of the lactone to the hydroxy-acid was confirmed by HPLC analysis and $^1H$ NMR spectroscopy.

EXAMPLE 2

Preparation of N-(2(R)-Amino-3-mercaptopropyl)isoleucyl-isoleucyl-homoserine lactone and N-(2(R)-Amino3-mercaptopropyl)-isoleucyl-isoleucyl-homoserine The title compounds were prepared according to the methods of Example 1, substituting N-t-butoxycarbonyl-isoleucine for the phenylalanine derivative used in Step A. The lactone was obtained as a solid, mp 111°–113° C. $^1H$ NMR (DMSO) δ8.66 (d,J=9 Hz, 1H), 8.49–8.28 (m, 1H), 4.61 (q, J=9 Hz, 1H), 4.36 (t, J=9 Hz, 1H), 4.31–4.15 (m, 2H), 3.50–3.34 (m, 2H), 3.00–2.71 (m, 4H), 2.45–2.30 (m, 1H), 2.30–2.17 (m, 1H), 1.85–1.4 (m, 5H), 1.22–1.05 (m, 2H), 0.97–0.74 (m, 12H). Anal. Calcd for $C_{19}H_{36}N_4O_4S.2CF_3COOH$: C, 42.85; H, 5.94; N, 8.69. Found: C, 43.00; H, 5.69; N, 8.89. The hydroxy acid was generated in situ according to Example 1, Step G.

EXAMPLE 3

Preparation of N-[N'-(2(R)-amino-3-mercaptopropyl)isoleucyl-isoleucyl] -3(S)-aminotetrahydropyran-2-one and N-[N'-(2(R)-amino-3-mercaptopropyl)isoleucyl-isoleucyl]-3(S)-amino-4-hydroxy-pentanoic acid Step A: Preparation of 3(S)-aminotetrahydropyran-2-one.

The method of Gong and Lynn (J. Org. Chem. 55, 4763 (1990)) was used to convert L-glutamic acid to 3(S)-amino-4-hydroxy-pentanoic acid. The crude product of this reaction was treated with di-t-butyl dicarbonate to obtain 3(S)-t-butoxycarbonylamino-4-hydroxy-pentanoic acid, which was converted to the title compound by reaction with EDC. The compound was purified by column chromatography on silica gel. $^1H$ NMR ($CDCl_3$) δ5.35 (1H, br s), 4.40 (m, 1H), 4.35 (2H, t, J=6 Hz), 2.60 (1H, m), 2.0 (2H, m), 1.61 (1H, m), 1.47 (9H, s).

Step B: Preparation of N-[N'-(2(R)-amino-3-mercaptopropyl)isoleucyl-isoleucyl] -3(S)-aminotetrahydropyran-2-one The product of Step A was converted to 3(S)-aminotetrahydropyran-2-one hydrochloride by treatment with HCl gas according to the method of Example 1, Step B. This intermediate was further transformed to the title compound using the methods of Example 1: mp 88–93. Anal. Calcd for $C_{20}H_{38}N_4O_4S \cdot 2CF_3COOH \cdot 0.5\ H_2O$: C, 43.17; H, 6.19; N, 8.39. Found: C, 43.19; H, 6.34; N, 8.59.

The lactone was converted to the hydroxy acid by the method of Example 1, Step G.

EXAMPLE 4

Preparation of N-[2(S)-(2(R)-amino-3-mercaptopropylamino)-3(S)-methylpentyl]isoleucyl-homoserine lactone Step A: Preparation of N-[2(S)-t-butoxycarbonylamino-3(S)-methylpentyl]isoleucyl homoserine lactone.

Isoleucyl homoserine was reductively alkylated with N-t-butoxycarbonyl-isoleucine aldehyde using the method of Example 1, Step D.

Step B: Preparation of N-[2(S)-(2(R)-amino-3-mercaptopropylamino)-3(S)-methylpentyl]isoleucyl-homoserine lactone and N-[2(S)-(2(R)-amino-3-mercaptopropylamino)-3(S)-methylpentyl]isoleucyl-homoserine.

The product of Step A was converted to the title lactone using the methods of Example 1, Steps D–F. The compound was obtained as a solid, mp 65°–69° C. Anal. Calcd for $C_{19}H_{38}N_4O_3S \cdot 3CF_3COOH$: C, 39.60; H, 5.65; N, 7.39. Found: C, 39.55; H, 5.45; N, 7.52.

The hydroxy acid was prepared in situ according to Example 1, Step G.

EXAMPLE 5

Preparation of N-[N'-(2(R)-amino-3-mercaptopropyl)isoleucyl-phenylalanyl] -3(S)-amino-tetrahydropyran-2-one and N-[N'-(2(R)-amino-3-mercaptopropyl)isoleucylphenylalanyl]-3(S)-amino-4-hydroxypentanoic acid The lactone form of the title compound was prepared using the procedure in Example 3, employing phenylalanine in place of isoleucine in the appropriate Step. The compound was isolated as a solid, mp 95°–100° C. Anal. Calcd for $C_{22}H_{36}N_4O_4S \cdot 2CF_3COOH \cdot 0.25Et_2O$: C, 47.28; H, 5.74; N, 7.88. Found: C, 47.63; H, 5.85; N, 8.11.

The hydroxy acid was prepared in situ according to Example 1, Step G.

EXAMPLE 6

Preparation of N-(2(R)-amino-3-mercaptopropyl)isoleucyl-phenylalanyl-homocysteine lactone Step A: Preparation of isoleucyl-phenylalanyl-homocysteine lactone N-t-butoxycarbonylisoleucyl-phenylalanine (496 mg) and 3-hydroxy-4-oxo-1,2,3-benzotriazine (320 mg) were dissolved in a mixture of DMF and methylene chloride and EDC (275 mg) was added. After 5 min homocysteine thiolactone hydrochloride (204 mg) and N-methyl morpholine (310 µl) were added. The reaction was stirred for 16 hours at room temperature and the solvent was removed in vacuo. The residue was partitioned between ethyl acetate and 10% citric acid solution. The organic phase was washed with saturated sodium bicarbonate solution and brine, dried ($Na_2SO_4$), filtered, and concentrated in vacuo. The solid residue was chromatographed on silica gel to give a white solid product. This solid was dissolved in cold 25% trifluoroacetic acid: methylene chloride. After 45 min the reaction mixture was concentrated in vacuo and the residue was purified by preparative reverse phase HPLC. Lyophilization gave the title compound as a white solid. NMR ($CDCl_3$+ $CD_3OD$) δ0.86 (m, 6H), 1.14 (m, 1H), 1.45 (m, 1H), 1.60–2.12 (br m, 7H), 2.18 (m, 1H), 2.48 (m, 1H), 3.05 (m, 1H), 3.12–3.34 (m, 3H), 3.86 (d, 1H), 4.35 (dd, 1H), 4.60 (m, 1H), 7.24 (m, 5H), 7.71 (d, 1H), 8.20 (d, 1H).

Step B: Preparation of N-[2(R)-amino-3-mercaptopropyl] isoleucyl-phenylalanyl homocysteine lactone N-(t-butoxycarbonyl)-S-triphenylmethylcysteine aldehyde (188 mg) as prepared in Example 1, Step C, and the product of Step A (201.8 mg) were dissolved in anhydrous ethanol (5 ml) under an argon atmosphere. 3 Å molecular sieves and 210 µl of 1M sodium cyanoborohydride in THF were added. The reaction mixture was stirred 16 hours, filtered and concentrated in vacuo. The residue was chromatographed on silica gel to give N-[2(R)-(t-butoxycarbonyl amino)-3-triphenylmethylmercaptopropyl]isoleucyl-phenylalanyl-homocysteine lactone as a solid intermediate. Further transformation by the method described in Example 1, Step F gave the title compound as a white solid, mp 82°–108° C. NMR ($CD_3OD$) δ0.76 (d, 3H), 0.86 (t, 3H), 1.09 (m, 1H), 1.48 (m, 1H), 1.58 (m, 1H), 2.20 (m, 1H), 2.58 (m, 2H), 2.68 (m, 2H), 2.78 (dd, 1H), 2.94 (m, 2H), 3.22 (m, 2H), 3.45 (m, 1H), 4.63 (dd, 1H), 7.24 (m, 1H), 7.30 (m, 4H). Anal. Calcd for $C_{22}H_{34}N_4O_3S_2 \cdot 2CF_3CO_2H$: C, 44.95; H, 5.22; N, 8.06. Found: C, 4.54; H, 4.97; N, 8.13.

EXAMPLE 7

Preparation of N-(2(R)-amino-3-mercaptopropyl)-isoleucyl-isoleucyl-homocysteine lactone Using the methods described in Example 2, substituting homocysteine for homoserine, the title compound was obtained as a lyophilized powder, mp 110°–112.7° C. $^1$H NMR ($CD_{3l\ OD}$) δ0.94 (m, 9H), 1.02 (d, 3H), 1.23 (m, 2H), 1.62 (m, 2H), 1.73 (m, 1H), 1.87 (m, 1H), 2.22 (m, 1H), 2.54 (m, 1H), 2.78 (dd, 1H), 2.86 (m, 3H), 3.08 (d, 1H), 3.41 (m, 1H), 4.30 (m, 1H), 4.62 (dd, 1H). Anal. Calcd for $C_{19}H_{36}N_4O_3S_2 \cdot 2CF_3CO_2H \cdot 0.8\ H_2O$: C, 40.92; H, 5.91; N, 8.30. Found: C, 40.86; H, 5.75; N, 8.49.

EXAMPLE 8

In vivo ras farnesylation assay

The cell line used in this assay was the v-ras line, which expressed vital Ha-ras p21. The assay was performed essentially as described in DeClue, J. E. et. al., Cancer Reasearch 51, 712–717, (1991). Cells in 10 cm dishes at 50–75% confluency were treated with the test compound (final concentration of solvent, methanol or dimethyl sulfoxide, was 0.1%). After 4 hours at 37° C., the cells were labelled in 3 ml methionine-free DMEM supplemeted with 10% regular DMEM, 2% fetal bovine serum and 400 µCi[$^{35}$S] methionine (1000 Ci/mmol). After an additional 20 hours, the cells were lysed in 1 ml lysis buffer (1% NP40/20 nnM HEPES, pH 7.5/5 mM $MgCl_2$/1 mM DTT/10 µg/ml aprotinen/2 µg/ml leupeptin/2 µg/ml antipain/0.5 mM PMSF) and the lysates cleared by centrifugation at 100,000×g for 45 min. Aliqouts of lysates containing equal numbers of acid-precipitable counts were brought to 1 ml with IP buffer (lysis buffer lacking DTT) and immunoprecipitated with the ras-specific monoclonal antibody Y13-259 (Furth, M. E. et al., J. Virol. 43, 294–304, (1982)). Following a 2 hour antibody incubation at 4° C., 200 µl of a 25% suspension of protein A-Sepharose coated with rabbit anti rat IgG was added for 45 min. The immunoprecipitates were washed four times with IP wash buffer (20 mM HEPES, pH 7.5/1 mM EDTA/ 1% Triton X-100/0.5% deoxycholate/0.1% SDS/0.1M NaCl), boiled in SDS-PAGE sample buffer and loaded on 13% acrylamide gels. When the dye front reached the bottom, the gel was fixed, soaked in Enlightening, dried and autoradiographed. The intensities of the bands corresponding to farnesylated and nonfarnesylated ras proteins were compared to determine the percent inhibition of farnesyl transfer to protein.

TABLE 1

Inhibition of Ras farnesylation by compounds of this invention in the v-ras cell line

| Compound | Inhibition |
| --- | --- |
| N-[2(S)-(2(R)-amino-3-mercaptopropyl-amino)-3(S)-methylpentyl]isoleucyl-homoserine | No Inhibition |
| N-[2(S)-(2(R)-amino-3-mercaptopropyl-amino)-3(S)-methylpentyl]isoleucyl-homoserine lactone | 90% Inhibition at 100 μM test concentration |

EXAMPLE 9

In vitro inhibition of Ras Farnesyl Transferase

Farnesyl-protein transferase (FTase) from bovine brain was chromatographed on DEAE-Sephacel (Pharmacia, 0–0.8M NaCl gradient elution), N-octyl agarose (Sigma, 0–0.6M Nacl gradient elution), and a mono Q HPLC column (Pharmacia, 0–0.3M NaCl gradient). Ras-CVLS at 3.5 μM, 0.25 μM [$^3$H]FPP, and the indicated compounds were incubated with this partially purified enzyme preparation. The FTase data presented below is a measurement of the ability of the test compound to inhibit Ras farnesylation in vitro.

TABLE 2

Inhibition of Ras farnesylation by compounds of this invention

| Compound | $IC_{50}$*(nM) |
| --- | --- |
| N-[2(S)-(2(R)-amino-3-mercaptopropyl-amino)-3(S)-methylpentyl]isoleucyl-homoserine | 12 |
| N-[2(S)-(2(R)-amino-3-mercaptopropyl-amino)-3(S)-methylpentyl]isoleucyl-homoserine lactone | 950 |
| N-[N'-(2(R)-amino-3-mercaptopropyl)-isoleucyl-isoleucyl]-3(S)-amino-4-hydroxy-pentanoic acid | 24 |
| N-[N'-(2(R)-amino-3-mercaptopropyl)-isoleucyl-isoleucyl]-3(S)-aminotetra-hydropyran-2-one | 470 |

*($IC_{50}$ is the concentration of compound which gives 50% inhibition of FTase under the described assay conditions)

What is claimed is:

1. A compound which inhibits farnesyl-protein transferase of the formula:

I wherein:

X and Y are independently $H_2$ or O, provided that at least one of these is $H_2$;

$R^1$ is an alkyl group, an acyl group, an alkylsulfonyl group or arylsulfonyl group, wherein the alkyl and the alkyl portion of the acyl is a straight chain or branched chain hydrocarbons of 1 to 6 carbon atoms, or in the alternative $R^1$NH may be absent;

$R^2$ and $R^3$ are independently selected from
 a) a side chain of naturally occurring amino acids;
 b) a aliphatic group selected from:
  i) allyl,
  ii) cyclohexyl, and.
  iii) a branched or unbranched saturated chain of 2 to 8 carbons;
   wherein the aliphatic group is optionally substituted with an aromatic or heteroaromatic ring;
 c) phenyl, and
 d) a heteroaromatic group selected from pyridyl and imidazolyl;

Z is O or S; and n is 0, 1 or 2;

or a pharmaceutically acceptable salt thereof.

2. A compound which inhibits farnesyl-protein transferase which is:

N-(2(R)-amino-3-mercaptopropyl)isoleucyl-phenylalanyl-homoserine lactone,

N-(2(R)-amino-3-mercaptopropyl)isoleucyl-isoleucylhomoserine lactone,

N-(2(R)-amino-3-mercaptopropyl)isoleucyl-phenylalanyl-homocysteine lactone,

N-[2(S)-(2(R)-amino-3-mercaptopropylamino)-3(S)-methyl pentyl]isoleucyl-homoserine lactone, N-[N'-(2(R)-amino-3-mercaptopropyl)isoleucyl-phenylalanyl]-3(S)-amino-tetrahydropyran-2-one, N-[N'-(2(R)-amino-3-mercaptopropyl)isoleucyl-isoleucyl]-3(S)-amino-tetrahydropyran-2-one, N-(2(R)-amino-3-mercaptopropyl)isoleucyl-isoleucylhomocysteine lactone.

3. A compound of claim 1 which is:

N-[2(S)-(2(R)-amino-3-mercaptopropylamino)-3(S)-methylpentyl]isoleucyl-homoserine lactone 4. A compound of claim 1 which is:

N-[N'-(2(R)-amino-3-mercaptopropyl)isoleucyl-isoleucyl]-3(S)-aminotetrahydropyran-2-one

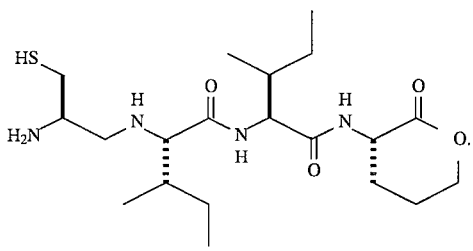

5. A chemotherapeutic composition comprising a pharmaceutical carrier, and dispersed therein, a therapeutically effective amount of compound of claim 1.

6. A chemotherapeutic composition comprising a pharmaceutical carrier, and dispersed therein, a therapeutically effective amount of compound of claim 2.

7. A chemotherapeutic composition comprising a pharmaceutical carrier, and dispersed therein, a therapeutically effective amount of compound of claim 3.

8. A chemotherapeutic composition comprising a pharmaceutical carrier, and dispersed therein, a therapeutically effective amount of compound of claim 4.

9. A method for inhibiting farnesylation of Ras protein which comprises administering to a mammal in need thereof a therapeutically effective amount of a composition of claim 5.

10. A method for inhibiting farnesylation of Ras protein which comprises administering to a mammal in need thereof a therapeutically effective amount of a composition of claim 6.

11. A method for inhibiting farnesylation of Ras protein which comprises administering to a mammal in need thereof a therapeutically effective amount of a composition of claim 7.

12. A method for inhibiting farnesylation of Ras protein which comprises administering to a mammal in need thereof a therapeutically effective amount of a composition of claim 8.

* * * * *